(12) United States Patent
Kessler et al.

(10) Patent No.: US 7,628,997 B1
(45) Date of Patent: *Dec. 8, 2009

(54) PRESERVATIVES FOR PERISHABLE PREPARATIONS, IN PARTICULAR FOR COSMETIC AND PHARMACEUTICAL PREPARATIONS

(75) Inventors: Susanne Kessler, Ergolding (DE); Sean Lee, Karlsruhe (DE)

(73) Assignee: Schott AG, Mainz (DE)

( * ) Notice: Subject to any disclaimer, the term of this patent is extended or adjusted under 35 U.S.C. 154(b) by 68 days.

This patent is subject to a terminal disclaimer.

(21) Appl. No.: 10/030,278

(22) PCT Filed: Jul. 7, 2000

(86) PCT No.: PCT/DE00/02231

§ 371 (c)(1),
(2), (4) Date: Apr. 9, 2002

(87) PCT Pub. No.: WO01/03650

PCT Pub. Date: Jan. 18, 2001

(30) Foreign Application Priority Data

Jul. 9, 1999 (DE) ............................ 199 32 239

(51) Int. Cl.
*A61K 8/19* (2006.01)
*A61K 91/14* (2006.01)
*A61K 8/20* (2006.01)
*A61K 8/27* (2006.01)
*A61K 9/20* (2006.01)

(52) U.S. Cl. ..................... 424/401; 424/400
(58) Field of Classification Search .............. 424/404, 424/401, 400
See application file for complete search history.

(56) References Cited

U.S. PATENT DOCUMENTS

| | | | |
|---|---|---|---|
| 4,014,995 A | 3/1977 | Juliano | |
| 4,155,870 A | 5/1979 | Lorgensen | |
| 5,074,916 A | 12/1991 | Hench et al. | |
| 5,290,544 A * | 3/1994 | Shimono et al. | ............... 424/63 |
| 5,762,950 A * | 6/1998 | Yli-Urpo et al. | ............ 424/422 |
| 5,766,611 A | 6/1998 | Shimono | |
| 5,834,008 A | 11/1998 | Greenspan et al. | |
| 2002/0086039 A1 * | 7/2002 | Lee et al. | .................... 424/401 |

FOREIGN PATENT DOCUMENTS

| | | |
|---|---|---|
| WO | 96 24364 A | 8/1996 |
| WO | 97/27148 | 7/1997 |
| WO | 98/11853 | 3/1998 |
| WO | WO 98/11853 * | 3/1998 |
| WO | WO 9811853 A1 * | 3/1998 |
| WO | 00/15167 | 3/2000 |
| WO | 00/76486 A1 | 12/2000 |

OTHER PUBLICATIONS

Allen et al, The Antibacterial Properties of a Bioactive Glass, Department of Microbiology and Peridontology, Eastman Dental Institute, London.*

Yamanaka et al., "Enzymatic Activity of Glucose Oxidase Encapsulated in Transparent Glass by the Sol-Gel Method," Chemistry of Materials, 4(3):495-497 (1992).*

Wu et al., "Bacteriorhodopsin Encapsulated in Transparent Sol-Gel Glass: A New Biomaterial," Chemistry of Materials, 5(1):115-120 (1993).*

Wang et al., "Affinity of Antifluorescein Antibodies Encapsulated Within a Transparent Sol-Gel Glass," Analytical Chemistry, 65(19):2671-2675 (1993).*

Yamanaka et al., "Enzymatic Activity of Glucose Oxidase Encapsulated in Transparent Glass by the Sol-Gel Method," Chemistry of Materials, 4(3):495-497 (1992).*

Wu et al.,."Bacteriorhodopsin Encapsulated in Transparent Sol-Gel Glass: A New Biomaterial," Chemistry of Materials, 5(1):115-120 (1993).*

Wang et al., "Affinity of Antifluorescein Antibodies Encapsulated Within a Transparent Sol-Gel Glass," Analytical Chemistry, 65(19):2671-2675 (1993).*

Yamanaka et al., "Enzymatic Activity of Glucose Oxidase Encapsulated n Transparent Glass by the Sol-Gel Method," Chemistry of Materials, 4(3):495-497(1992).*

(Continued)

*Primary Examiner*—Johann R Richter
*Assistant Examiner*—Courtney Brown
(74) *Attorney, Agent, or Firm*—Michael J. Striker

(57) ABSTRACT

The method of preserving a perishable cosmetic and/or pharmaceutical preparation includes adding bioactive glass particles to the preparation, preferably in amounts up to 10 percent by weight. The bioactive glass particles preferably have particle sizes ($d_{50}$) less than or equal to 10 μm and contain from 40 to 60 wt. % $SiO_2$, 10 to 30 wt. % CaO, 10 to 35 wt. % $Na_2O$, 2 to 8 wt. % $P_2O_5$, 0 to 25 wt. % $CaF_2$, 0 to 10 wt. % $B_2O_3$, 0 to 8 wt. % $K_2O$ and/or 0 to 5 wt. % MgO. A liquid cosmetic preparation with alcohol content insufficient for preservation is preserved in an inconspicuous manner by adding bioactive glass particles with particle sizes less than or equal to 10 μm and with a refractive index close enough to that of the liquid cosmetic preparation so that bioactive glass particles are substantially invisible to an observer.

13 Claims, No Drawings

OTHER PUBLICATIONS

Wu et al., "Bacteriorhodopsin Encapsulated in Transparent Sol-Gel Glass: A New Biomaterial," Chemistry of Materials, 5(1):115-120 (1993).*

Wang et al., "Affinity of Antifluorescein Antibodies Encapsulated Within a Transparent Sol-Gel Glass," Analytical Chemistry, 65(19):2671-2675 (1993).*

Patent Abstracts of Japan vol. 0152, No. 78, Jul. 15, 1991 & JP 03 095516 A, Apr. 16, 1991.

Patent Abstracts of Japan vol. 1998, No. 10, Aug. 31, 1998 & JP 10 139644 A, May 26, 1998.

Larry L. Hench and John K. West: "Biological Applications of Bioactive Glasses" Life Chemistry Reports 1996, vol. 13, p. 187-241.

"An Introduction to Bioceramic" L. Hench and J. Wilson, Eds. World Scientific, NJ 1993, pp. 41-63.

John E. Rectenwald et al: "Bioglass Elicits an Anti-Inflammatory Response . . . ", Infection and Immunity, 19. Annual Meeting, Surgical Infection Society 1999 28.4-01.05.1999, pp. 2-21.

J. Allen et al: "Antibacterial Properties of a Bioactive Glass", Departments of Microbiology and Peridontology, Eastman Dental Institute, London.

Chemical Abstracts 63-Pharmaceuticals, vol. 129, No. 16, 1998, p. 1038.

Larry Hench: "Bioceramics: From Concept of Clinic" J. Am. Ceram. Soc. 74 (7), 1991, pp. 1487-1510.

* cited by examiner

PRESERVATIVES FOR PERISHABLE PREPARATIONS, IN PARTICULAR FOR COSMETIC AND PHARMACEUTICAL PREPARATIONS

DESCRIPTION

The invention relates to preservatives and to their use for preserving perishable preparations, particularly cosmetic and pharmaceutical compositions.

It is known to treat many perishable goods, such as foodstuffs, drugs etc. with chemical and particularly organo-chemical preservatives to extend their useful life.

This is particularly true also for cosmetic preparations that come in contact with the skin. In this case, namely during application to the skin or, in particular, when the preparation is manually removed from the jar or during the use of a lipstick, bacteria are introduced into the preparations. In the skin-compatible environment prevailing in cosmetic preparations, bacteria introduced in this manner can undergo rapid multiplication so that even after a few days their concentration can become intolerably high. The same problem also arises with cosmetic preparations stored in bottles or tubes. Although in this case, because of less contact with the skin, contamination with bacteria during removal from the container is less pronounced, contact of bacteria-bearing skin with the preparation cannot be avoided and, hence, these forms of application are also subject to rapid contamination. For this reason, it is necessary to provide such commercial preparations with bactericides or bacteriostatic agents. Such substances, however, are cytotoxic and, furthermore, are allergenic in a large number of individuals.

To ensure proper manufacturing practice worldwide, in 1968 WHO issued "Good Manufacturing Practice" (GMP). According to these guidelines, product hygiene and quality control, among other things, are to be ensured and impurities avoided. In the meantime, the GMP has been complemented by "Good Storage Practice" (GSP), valid particularly in the pharmaceutical and cosmetic industries, to ensure proper product storage.

Thus, according to U.S. Pat. No. 5,766,611, an attempt has been made to use as a preservative a soluble glass that release silver, zinc and/or copper. These substances released by the glass also act as cell poisons and thus are cytotoxic. Hence, constant contact with such a preservative is not safe.

It is already known to use bioactive glass for oral care. For example, tooth pastes are known which promote the remineralization of teeth. U.S. Pat. No. 5,834,008 describes the use of bioglass for healing wounds. For example, by the application of this type of glass, it is possible to bring about the healing of non-healing, ulcerating wounds, particularly in diabetics and stroke patients.

J. Allen, H. Neumann and M. Wilson described the inhibition of bacterial colonization by using Bioglas® 45 S 5 with a particle size of 355-500 µm. Normal glass beads (window glass) with a comparable particle size of 455-600 µm showed no antibacterial action.

The essential properties of bioactive glass are known to those skilled in the art and are described, for example, in U.S. Pat. No. 5,074,916. According to this patent, bioactive glass differs from conventional lime-sodium silicate glasses in that it binds to living tissues.

Bioactive glass is available in the United States, for example under the tradename "Bioglas®", from US Biomaterials Corp., Alachua,. Fla. 32615, USA. This is a glass which in contact with an organism undergoes a special biological reaction. In contact with a body fluid, it exchanges ions with this fluid. This ion exchange causes the release of sodium ions and calcium ions which within a few minutes form on the glass a layer of silica gel leading to the formation of a hydroxy-carbonate-apatite layer which is identical to the mineral phase of bone. Hydroxy-carbonate-apatite is then formed, and the cells form collagen which becomes embedded in this layer. This produces a physico-chemical bond between the bioactive glass and the tissue or the bone material, which brings about faster bone regeneration. In this regard, it has been shown in animal studies that Bioglas® is nearly as effective as the transplantation of parts of a person's own bone.

The use of bioactive glass in combating acne is also known. To this end, a preparation containing bioactive glass is applied to the areas affected by acne, which has a positive effect on the inflammations. Also to be mentioned in this regard are the publications by John E. Rectenwald, L. L. Moldawer, Sean Lee et al. in Infection and Immunity (submitted for publication) and [Proceedings of the] 19th Annual Meeting of the Surgical Infection Society, Seattle, Apr. 29 to May 1, 1999, which state that bioglass brings about the formation or secretion of the inflammation-inhibiting hormone interleukin 6 (IL 6) and suppresses the inflammation-promoting cytokines TNF-α, IL-1-α and IL-10.

Moreover, E. Allen et al. (Department of Microbiology and Periodontology, Eastman Dental Institute) reported that the bioactive glass Bioglas® 45-S-5 obtainable from U.S. Biomaterials, Alachua, Fla. 32615, USA, exhibits antibacterial activity not shown by normal glass beads (window glass).

Hence, the object of the invention is to provide a preservative agent which in contrast to previously known agents exerts no negative application effects, particularly when applied to the skin.

According to the invention, this objective is reached by means of a preservative containing bioactive glass.

Bioactive glasses have been known for a long time and have been described in summary form, for example, by Larry L. Hench and John. K. West in "Biological Applications of Bioactive Glasses", Life Chemistry Reports 1996, vol. 13, pp. 187-241, or in "An Introduction to Bioceramics", L. Hench and J. Wilson, eds., World Scientific, New Jersey (1993). Bioactive glasses, in contrast to conventional glasses, are characterized in that they are soluble in aqueous media and that they form a layer of hydroxyapatite on their surface. Most current bioactive glasses are prepared either as fusible glass, in which case they contain much less $SiO_2$ and much more sodium than normal window or bottle glasses, or they are sol-gel glasses which then, in contrast to fusible glasses, contain a high amount of silicon oxide and a small amount of sodium or no sodium at all.

Bioactive silicon-containing glass or bioactive glass is a material which comprises silicon oxide or silicon hydroxide and which facilitates the formation and transfer of SiOH groups. Hence, bioactive silicon-containing glass can be, for example, a bioactive glass derived from a mixture of silicon oxide or silicon hydroxide and one or more elements of the group comprising sodium, potassium, calcium, magnesium, boron, titanium, aluminum as well as anions containing nitrogen, phosphorus and fluorine. Moreover, it can be, for example, a sodium silicate of the water glass type or silica gel or a SiOH groups-containing solution or a silicon oxide or silicon hydroxide comprising hydroxyapatite as well as a silica gel containing calcium and phosphorus. One of the essential common features of bioactive silica gel-containing glass is its ability to form and to transfer SiOH groups. Moreover, it contains calcium ions and phosphate ions.

The bioactive glass contained according to the invention is preferably a conventional bioactive glass, well known to those skilled in the art. Such glasses usually contain $SiO_2$, a high amount of $Na_2O$ and CaO as well as phosphorus, the latter in a high molar ratio of calcium to phosphorus, said ratio in most, but not necessarily all, cases having a value of about five. When such bioactive glasses come in contact with water or with a body fluid, they give rise to special reactions, namely the sodium and calcium ions of the glass are exchanged for $H^+$ ions from the solution by a cation-exchange reaction. As a result, a silanol groups-presenting surface is formed on which sodium hydroxide and calcium hydroxide accumulate. The increase in hydroxyl ion concentration at the glass surface now brings about a further reaction with the $SiO_2$ network giving rise to additional silanol groups which can also lie more deeply in the glass.

Because of the high, alkaline pH in the interstitial glass space, a mixed hydroxyapatite phase is formed from CaO and $P_2O_6$ and crystallizes on the $SiO_2$ surface. In biological materials, this phase binds to mucopolysaccharides, collagens and glycoproteins.

The molar ratio of calcium to phosphorus is preferably >2 and particularly >3 and preferably <30 and particularly <20, a ratio of <10 being particularly preferred.

Particularly preferred are preservatives with bioactive glass particles containing $SiO_2$, CaO, $Na_2O$, $P_2O_6$, $CaF_2$, $B_2O_3$, $K_2O$ and/or MgO. If the preservative agent contains bioactive particles of fusible glass, these particles preferably contain 40-60 wt. % of $SiO_2$, 10-30 wt. % of CaO, 10-35 wt. % of $Na_2O$, 2-8 wt. % of $P_2O_6$, 0-25 wt. % of $CaF_2$, 0-10 wt. % of $B_2O_3$, 0-8 wt. % of $K_2O$ and/or 0-5 wt. % of MgO, based on the total weight of the glass.

If the bioactive glass is a fusible glass, then the upper limit of the silicon dioxide it contains is 60 wt. % and preferably 55 wt. %, an upper limit of 50 wt. % being particularly preferred. The sodium oxide content is preferably higher than 15 wt. % and particularly higher than 18 wt. %. A sodium oxide content of >20 wt. % is particularly preferred.

If the bioactive glass contained in the preservative of the invention has been produced by the sol-gel process, its silicon dioxide content can be significantly higher than in fusible glasses and its sodium oxide content can be nil. Bioactive glasses made by the sol-gel process preferably contain 40 to 90 wt. % of $SiO_2$, 4 to 45 wt. % of CaO, 0 to 10 wt. % of $Na_2O$, 2 to 16 wt. % of $P_2O_6$, 0 to 25 wt. % of $CaF_2$, 0 to 4 wt. % of $B_2O_3$, 0 to 8 wt. % of $K_2O$ and/or 0 to 5 wt. % of MgO.

The phosphorus oxide content of both previously described kinds of bioactive glass is preferably at least 2 wt. % and particularly at least 4 wt. %.

In a preferred embodiment of the invention, the soluble bioactive glass does not contain or release toxic metal cations such as $Ag^+$, $Cu^{2+}$, $Cu^+$ and/or $Zn^{2+}$ etc. in toxic concentrations. To achieve synergistic effects, however, it may in some cases be desirable to add also a biocidal glass that does release toxic cations.

The bioactive glass itself is a material having a more or less round shape like, for example, sand. Such particles can have a size of up to about 0.5-1 mm, but preferably are substantially smaller. The common particle size is ≦400 μm and particularly ≦200 μm, particles having a size of ≦100 μm, preferably ≦90 μm and particularly ≦60 μm or ≦20 μm being especially advantageous. Preferred particles have a diameter $d_{50}$ of ≦10 μm, preferably ≦5 μm and particularly ≦2 μm. The higher the surface-to-weight or surface-to-volume ratio, the higher is the biocidal activity of the particles.

In a preferred embodiment of the invention, the bioactive glass is used to preserve cosmetic preparations. Preferred for this purpose is a fine-particle bioactive glass with particle size $d_{50}$≦5 μm and particularly ≦2 μm. Preferred cosmetic preparations are, in particular, creams, make-up compositions, lipsticks as well as lotions and ointments. Preferably no organic preservatives are present in the preparations, especially those that can cause negative application effects, such as cytotoxic and/or allergenic reactions. the moisture contained in these preparations further enhances the microbicidal activity of the bioactive glass.

The biocidal preservative of the invention is contained in the preparation to be preserved preferably in an amount of up to 25 wt. % and particularly up to 10 wt. %, based on the solids content of the preparation to be preserved. Upper limits of 7 wt. % or 5 wt. %, however, are preferred, 3 wt. % being particularly preferred. The lower limit values are 0.01 wt. % and particularly 0.1 wt. %, with 0.5 wt. % or 1 wt. % particularly preferred as the lower limit of the effective amount.

Surprisingly, we have now found that such preparations can be preserved with bioactive glass in an outstanding manner without it being necessary to add skin-irritating, cytotoxic or sometimes allergenic chemical preservatives. Moreover, an additional care effect is achieved as a result of the ability of bioactive glass to promote healing and particularly also to inhibit inflammation.

In special cases, however, it may be desirable to add the preservative of the invention to preparations rendered storage-stable with a common preservative so as to achieve a synergistic effect.

The preservative is preferably added to a proton-containing solvent, particularly to an aqueous and/or alcoholic solvent. It is also possible, however, to use the preservative in an aprotic solvent provided such a medium allows the release of the soluble cations of the glass. Preferred aprotic solvents are ketones such as acetone, fats, waxes, oils and the corresponding liquid or solid hydrocarbons. The preservative of the invention is also particularly well suited for preserving water-in-oil and oil-in-water emulsions.

Liquid cosmetic preparations with an alcohol content insufficient for preservation can also be preserved with bioactive glass. In this case, it is preferred to use a glass with a refractive index equal to that of the liquid. In this manner, the added glass is "invisible" to the consumer. To achieve a cosmetic effect, however, the glass can intentionally be made visible in a desired manner, for example by coloring.

The invention claimed is:

1. In a method of preserving a perishable cosmetic preparation, the improvement comprising adding from 0.1 to 25 percent by weight of bioactive glass particles with particles sizes ($d_{50}$) up to about 10 μm to said perishable cosmetic preparation, so that upon contact with an aqueous medium said bioactive glass particles form a hydroxyapatite layer on surfaces of said bioactive glass particles and said bioactive glass particles thus provide antimicrobial action in said perishable cosmetic preparation because of the presence of said hydroxyapatite layer; and in which said bioactive glass particles contain calcium and phosphorus in a molar ratio greater than 2 and in relative amounts that are sufficient for formation of said hydroxyapatite layer on contact with said aqueous medium and said bioactive glass particles do not contain any $Ag^+$, $Cu^{+2}$, $Cu^+$ or $Zn^+$ cations.

2. The improvement as defined in claim 1, wherein said bioactive glass particles consist of from 40 to 60 percent by weight $SiO_2$, from 10 to 30 percent by weight CaO, from 10 to 35 percent by weight $Na_2O$, from 2 to 8 percent by weight $P_2O_5$, from 0 to 25 percent by weight of $CaF_2$, from 0 to 10 percent by weight $B_2O_3$, from 0 to 8 percent by weight of $K_2O$, and from 0 to 5 percent by weight MgO.

3. The improvement as defined in claim 1, wherein said bioactive glass particles consist of from 40 to 90 percent by weight $SiO_2$, from 4 to 45 percent by weight CaO, from 0 to 10 percent by weight $Na_2O$, from 2 to 16 percent by weight $P_2O_5$, from 0 to 25 percent by weight of $CaF_2$, from 0 to 4 percent by weight $B_2O_3$, from 0 to 8 percent by weight of $K_2O$, and from 0 to 5 percent by weight MgO.

4. The improvement as defined in claim 1, wherein said particles sizes ($d_{50}$) of said bioactive glass particles are less than or equal to 5 µm and said cosmetic composition contains from 1 percent by weight to 10 percent by weight of said bioactive glass particles.

5. The improvement as defined in claim 1, wherein said perishable cosmetic composition contains an aqueous solvent or an alcoholic solvent.

6. In a perishable cosmetic preparation, the improvement comprising including from 0.1 to 25 percent by weight of bioactive glass particles with particles sizes ($d_{50}$) up to about 10 µm in said perishable cosmetic preparation, so that upon contact with an aqueous medium said bioactive glass particles form a hydroxyapatite layer on surfaces of said bioactive glass particles and said bioactive glass particles thus provide antimicrobial action in said perishable cosmetic preparation due to the presence of said hydroxyapatite layer; and in which said bioactive glass particles contain calcium and phosphorus in a molar ratio greater than 2 and in relative amounts that are sufficient for formation of said hydroxyapatite layer on contact with said aqueous medium and said bioactive glass particles do not contain any $Ag^+$, $Cu^{+2}$, $Cu^+$ or $Zn^+$ cations.

7. The improvement as defined in claim 6 and further comprising not including skin-irritating chemical preservatives or allergenic chemical preservatives in said perishable cosmetic preparation.

8. The improvement as defined in claim 6, wherein said bioactive glass particles consist of from 40 to 60 percent by weight $SiO_2$, from 10 to 30 percent by weight CaO, from 10 to 35 percent by weight $Na_2O$, from 2 to 8 percent by weight $P_2O_5$, from 0 to 25 percent by weight of $CaF_2$, from 0 to 10 percent by weight $B_2O_3$, from 0 to 8 percent by weight of $K_2O$, and from 0 to 5 percent by weight MgO.

9. The improvement as defined in claim 6, wherein said bioactive glass particles consist of from 40 to 90 percent by weight $SiO_2$, from 4 to 45 percent by weight CaO, from 0 to 10 percent by weight $Na_2O$, from 2 to 16 percent by weight $P_2O_5$, from 0 to 25 percent by weight of $CaF_2$, from 0 to 4 percent by weight $B_2O_3$, from 0 to 8 percent by weight of $K_2O$, and from 0 to 5 percent by weight MgO.

10. The improvement as defined in claim 6, wherein said particles sizes ($d_{50}$) of said bioactive glass particles are less than or equal to 5 µm and said cosmetic composition contains from 1 percent by weight to 10 percent by weight of said bioactive glass particles.

11. The improvement as defined in claim 6, wherein said perishable cosmetic composition contains an aqueous solvent or an alcoholic solvent.

12. The improvement as defined in claim 1, wherein said particles sizes ($d_{50}$) are less than or equal to 5 µm.

13. The improvement as defined in claim 6, wherein said particles sizes ($d_{50}$) are less than or equal to 5 µm.

\* \* \* \* \*